United States Patent
Ito et al.

(10) Patent No.: US 7,960,483 B2
(45) Date of Patent: Jun. 14, 2011

(54) ADAMANTANE DERIVATIVE, COMPOSITION COMPRISING THE DERIVATIVE, AND OPTICAL AND ELECTRONIC MEMBER USING THE COMPOSITION

(75) Inventors: Hajime Ito, Chiba (JP); Yasunari Okada, Chiba (JP); Hideki Yamane, Chiba (JP); Nobuaki Matsumoto, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 249 days.

(21) Appl. No.: 12/279,772

(22) PCT Filed: Feb. 1, 2007

(86) PCT No.: PCT/JP2007/051681
§ 371 (c)(1),
(2), (4) Date: Aug. 18, 2008

(87) PCT Pub. No.: WO2007/094173
PCT Pub. Date: Aug. 23, 2007

(65) Prior Publication Data
US 2009/0062481 A1 Mar. 5, 2009

(30) Foreign Application Priority Data
Feb. 17, 2006 (JP) .................. 2006-040155

(51) Int. Cl.
*C08G 59/06* (2006.01)
*C08G 59/42* (2006.01)
*C08G 59/50* (2006.01)
*C08G 59/62* (2006.01)
*C08L 63/00* (2006.01)
*F21V 7/04* (2006.01)

(52) U.S. Cl. ........ 525/524; 362/612; 525/480; 525/481; 525/533; 525/534; 528/95; 528/97; 528/212

(58) Field of Classification Search ........................ None
See application file for complete search history.

(56) References Cited

U.S. PATENT DOCUMENTS
3,795,658 A * 3/1974 Thompson ............... 528/97
(Continued)

FOREIGN PATENT DOCUMENTS
JP          4 39665         2/1992
(Continued)

OTHER PUBLICATIONS

A., Beridze L. et al., "Cardo polycondensation polymers from 2, 2-bis (4-hydroxyphenyl) adamantane", Sint. Svoistva Nek. Nov. Polim. Mater., pp. 19-30, vol. 83, No. 115498, (1974).

Primary Examiner — Robert Sellers
(74) Attorney, Agent, or Firm — Oblon, Soivak, McClelland, Maier & Neustadt, L.L.P.

(57) ABSTRACT

An adamantane derivative of formula (I), a compound of formula (VII) or (VIII), compositions containing them, and optical electronic members using the resin compositions. In the formulas, W represents, for example, a hydrogen atom, X is bonded to a bridge-head adamantane carbon and represents, for example, a group of represented by the general formula (II), Y represents a group of formula (V) or (VI), $R^1$ represents a methyl group or an ethyl group, $R^2$ represents a $C_1$ to $C_{10}$ hydrocarbon group which may contain O or S, m is an integer of 2 to 4, k is an integer of 0 to (16−m) and p and q are each an integer of 1 to 5.

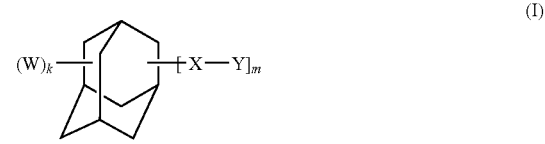

(I)

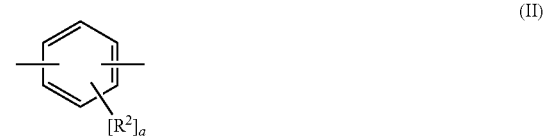

(II)

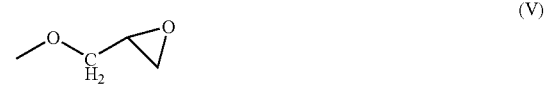

(V)

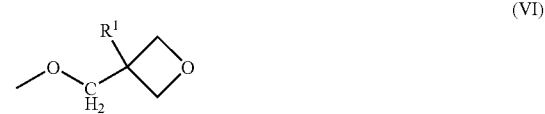

(VI)

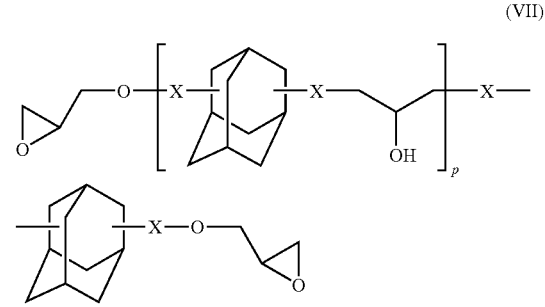

(VII)

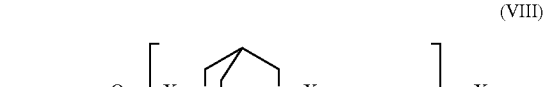

(VIII)

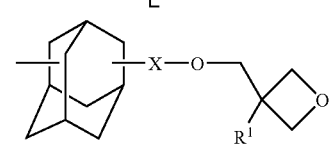

20 Claims, No Drawings

U.S. PATENT DOCUMENTS

| | | | |
|---|---|---|---|
| 6,066,711 A | 5/2000 | Hanazawa et al. | |
| 6,087,513 A | 7/2000 | Liao et al. | |
| 6,720,460 B2 * | 4/2004 | Yoshikawa et al. | 568/719 |

FOREIGN PATENT DOCUMENTS

| | | | |
|---|---|---|---|
| JP | 6 305044 | | 11/1994 |
| JP | 9 302077 | | 11/1997 |
| JP | 10 130371 | | 5/1998 |
| JP | 10-130371 A | * | 5/1998 |
| JP | 2003 321530 | | 11/2003 |
| JP | 2006 307062 | | 11/2006 |
| JP | 2006-307062 A | * | 11/2006 |
| JP | 2006 307063 | | 11/2006 |
| JP | 2006-307063 A | * | 11/2006 |
| WO | 99 62894 | | 12/1999 |

* cited by examiner

ADAMANTANE DERIVATIVE, COMPOSITION COMPRISING THE DERIVATIVE, AND OPTICAL AND ELECTRONIC MEMBER USING THE COMPOSITION

TECHNICAL FIELD

The present invention relates to a novel adamantane derivative, novel epoxy and oxetane compounds having an adamantane skeleton, compositions containing them, an optical electronic member and a sealant for an electronic circuit and, more specifically, to an adamantane derivative, an epoxy compound, an oxetane compound and a composition containing them, which can be used as a sealant for an electronic circuit (such as a sealant for an optical semiconductor or an organic electroluminescence (EL) device), as an optical electronic member (such as an optical wave guide, an optical communication lens or an optical film) and as an adhesive for them, and to an optical electronic member and a sealant for an electronic circuit using such a composition.

BACKGROUND ART

Adamantane is a stable, highly symmetrical compound in which four cyclohexane rings are condensed to form a cage-like structure. It is known that adamantane derivatives, which show peculiar functions, are useful as raw materials for medical materials and highly functional industrial materials. Further, because an adamantane compound has specific optical characteristics and heat resistance, an attempt has been made to use it as, for example, an optical disc substrate, an optical fiber or a lens (see, for example, Patent Documents 1 and 2). Further, an attempt has been made to use an adamantane ester as a raw material resin for a photoresist by utilizing its acid-sensitive property, dry etching resistance and transparency to UV light (see, for example, Patent Document 3).

In recent years, studies have been progressing for high precision, wider viewing angle and enhanced image quality of a flat panel display using a liquid crystal, an organic electroluminescence (EL) device and the like, for higher intensity, shorter wavelength and whitening of a light source using a light emitting diode (optical semiconductor) such as LED and the like, for higher frequency of an electronic circuit and for higher performance and improvement of an optical or electronic component such as an optical circuit or communication.

As a method for such an improvement, there have been investigated and developed basic materials such as a liquid crystal material and a light emitting material for an organic EL device. Investigation has also been made to seek higher performance of a resin that is used along with those basic materials as a coating material, a sealant or an adhesive. As a resin used for a coating material, a sealant or an adhesive of an optical or electronic component, various kinds of thermosetting resins, light-curable resins and thermoplastic resins have been applied. Such resins have been used in accordance with their respective characteristics by themselves such as heat resistance, transparency, solubility and adhesiveness.

In the field of LED which is advanced in terms of high performance, an illumination and a light using a white LED composed of a near ultra violet or blue light emitting device have been proposed and developed for practical use. In addition, it is expected that they will be developed to be used for home lighting and automobiles in the future. In an LED device, an inorganic semiconductor is sealed with a resin containing a fluorescent material. In this case, a conventional thermosetting resin such as a bisphenol A epoxy resin has limitation in heat resistance and light resistance. Thus there is a demand for a sealant which can fulfill the required characteristics (see, for example, Non-Patent Document 1).

Further, in the display field, an organic EL device of small size, high precision and energy saving is used. Also employed is an organic EL device of a top emission type. Accordingly, a sealing resin for use in an organic EL device is required not only to have a function of bonding a conventional sealing board such as stainless steel to a glass substrate and a function as a gas barrier, but also to exhibit, by itself, transparency, light resistance, heat resistance, mechanical strength, etc. (see, for example, Non-Patent Document 2).

Further, in the field of an electronic circuit integrated with a semiconductor, etc., an increase in volume of information and in communication speed and miniaturization of a device have been developed with the progress of an information-oriented society. Thus, further miniaturization, integration and increase of frequency are demanded. Furthermore, an optical circuit using an optical wave guide, etc. that enables higher speed processing has also been investigated. When a customarily employed resin such as a bisphenol A epoxy resin is used as a sealing resin or a resin for a film or a lens for the above circuits, the following problems are caused. Namely, in the case of an electronic circuit, the dielectric constant increases and heat resistance becomes insufficient. In the case of the optical wave guide and LED sealing, a reduction of transparency and yellow coloring of the resin by deterioration thereof due to light absorption by aromatic rings are caused.

Further, when a customarily employed resin such as a bisphenol A epoxy resin is used as an electric or electronic material, and when a cured product thereof has a high chlorine content, chlorine ions are formed by hydrolysis in moistened conditions. Because chlorine ions cause a reduction of electric insulation and a corrosion of the electric circuit, there is a demand for a low chlorine content epoxy resin.

On the other hand, a polymer compound having an adamantane skeleton is excellent in heat resistance. A polyester and a polycarbonate using an adamantane diol, for example, are known as such polymer compounds. Also, as a resin composition using an adamantane, there are disclosed a resin composition containing 1,3-bis(glycidyloxyphenyl) adamantane (see, for example, Patent Document 4) and a resin composition containing 2,2-bis(glycidyloxyphenyl)adamantane (see, for example, Patent Document 5). Although these resin compositions show a lowered dielectric constant and an improved transparency as compared with a bisphenol A epoxy resin, there are caused problems that these resins, which are crystalline compounds with high melting points, have poor compatibility with other epoxy resins and poor solubility in solvents and, therefore, have poor workability and cannot be used in an amount required to obtain a desired performance.

[Patent Document 1] Japanese Unexamined Patent Application Publication No. H06-305044

[Patent Document 2] Japanese Unexamined Patent Application Publication No. H09-302077

[Patent Document 3] Japanese Unexamined Patent Application Publication No. H04-39665

[Non-Patent Document 1] Monthly "Material Stage," June 2003, pages 20 to 24
[Non-Patent Document 2] Monthly "Material Stage," March 2003, pages 52 to 64
[Patent Document 4] Japanese Unexamined Patent Application Publication No. 2003-321530
[Patent Document 5] Japanese Unexamined Patent Application Publication No. H10-130371

DISCLOSURE OF THE INVENTION

Problems to be Solved by the Invention

In view of the above-mentioned circumstances, the present invention has as its objects the provision of an adamantane derivative, epoxy and oxetane compounds having an adamantane skeleton, compositions containing them capable of providing a cured product which has excellent optical properties such as transparency and light resistance, long-term heat resistance and electric characteristics such as dielectric permittivity, and which can be used as a sealant for an electronic circuit (such as a sealant for an optical semiconductor or an organic electroluminescence (EL) device), as an optical electronic member (such as an optical wave guide, an optical communication lens or an optical film) and as an adhesive for them, and the provision of an optical electronic member and a sealant for an electronic circuit using such compositions.

Means for Solving the Problem

The present inventors have made extensive studies with a view toward accomplishing the above objects and, as a result, have found that a composition affording a cured product suitable as an optical electronic member and a sealant for an electronic circuit can be obtained by using a specific adamantane derivative and an epoxy compound or an oxetane compound having a specific adamantane skeleton. The present invention has been completed based on the above finding.

Namely, the present invention provides the following adamantane derivative, an epoxy compound and an oxetane compound having an adamantane skeleton, compositions containing them, and an optical electronic member and a sealant for an electronic circuit using such compositions.

1. An adamantane derivative represented by the following general formula (I):

[Chemical Formula 1]

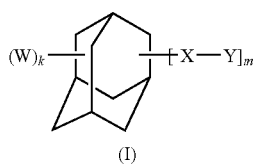

(I)

[wherein W represents a group selected from an alkyl group, a halogen atom, a hydroxyl group and =O formed by two W's taken together, X represents a group represented by the following general formula (II), (III) or (IV):

[Chemical Formula 2]

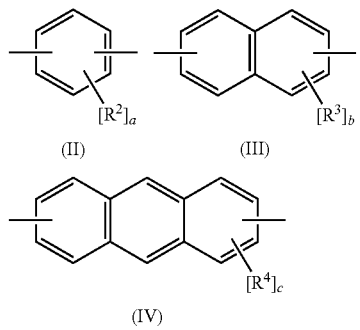

(where $R^2$ to $R^4$ each independently represent a $C_1$ to $C_{10}$ hydrocarbon group which may contain an oxygen atom or a sulfur atom, a represents an integer of 1 to 4, b represents an integer of 0 to 6 and c represents an integer of 0 to 8), Y represents a group represented by the following formula (V) or the following general formula (VI):

[Chemical Formula 3]

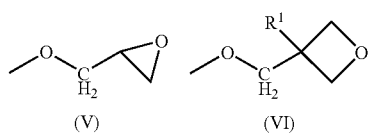

(where $R^1$ represents a methyl group or an ethyl group), m represents an integer of 2 to 4 and k represents an integer of 0 to (16−m)].

2. The adamantane derivative as defined in above 1, wherein X is attached to a bridge-head carbon of the adamantane skeleton.

3. The adamantane derivative as defined in above 1, wherein, in the general formula (I), m is 2 and each X is attached to the same methylene carbon of the adamantine skeleton.

4. The adamantane derivative as defined in any one of above 1 to 3, wherein, in the general formula (I), X is a group represented by the general formula (II).

5. An epoxy compound with an adamantane skeleton represented by the following general formula (VII):

[Chemical Formula 4]

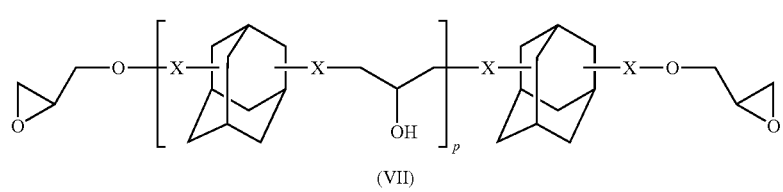

(VII)

[wherein X represents a group represented by the above general formula (II), (III) or (IV) and p represents an integer of 1 to 5].

6. An oxetane compound with an adamantane skeleton represented by the following general formula (VIII):

[Chemical Formula 5]

$$\text{(VIII)}$$

[wherein X represents a group represented by the above general formula (II), (III) or (IV), $R^1$ represents a methyl group or an ethyl group, and q represents an integer of 1 to 5].

7. The adamantane derivative as defined in any one of above 1 to 4, the epoxy compound as defined in above 5 or the oxetane compound as defined in above 6, having a total chlorine content of 2,000 ppm by mass or less.

8. A process for producing an adamantane derivative represented by the following general formula (I):

[Chemical Formula 8]

$$(W)_k\text{—[Adamantane]—}[X\text{—}Y]_m$$

(I)

[wherein W, X, Y, k and m are as defined below],
said process comprising reacting a phenolic hydroxyl group-containing adamantane derivative represented by the following general formula (a):

[Chemical Formula 6]

$$(W)_k\text{—[Adamantane]—}[X\text{—}OH]_m$$

(a)

[wherein W represents a group selected from an alkyl group, a halogen atom, a hydroxyl group and =O formed by two W's taken together, X represents a group represented by the above general formula (II), (III) or (IV), m represents an integer of 2 to 4 and k represents an integer of 0 to (16−m)] with a reactive cyclic ether represented by the following general formula (b):

Y'-D    (b)

[where Y' represents a group represented by the following formula (V') or the following general formula (VI'):

[Chemical Formula 7]

(V')    (VI')

(where $R^1$ represents a methyl group or an ethyl group) and D represents a group reactive with the phenolic hydroxyl group],
in the presence of an alkaline catalyst.

9. The process for producing an adamantane derivative as defined in above 8, wherein a reaction mixture obtained by the reaction of the adamantane derivative represented by the general formula (a) and the reactive cyclic ether compound represented by the general formula (b) is treated with an alkali metal hydroxide or an alkaline earth metal hydroxide.

10. The process for producing an adamantane derivative as defined in above 8, wherein a reaction mixture obtained by the reaction of the adamantane derivative represented by the general formula (a) and the reactive cyclic ether compound represented by the general formula (b) is subjected to crystallization to collect a purified product.

11. A composition of matters comprising at least one member selected from the group consisting of the adamantane derivative as defined in any one of above 1 to 4, the epoxy compound as defined in above 5 and the oxetane compound as defined in above 6, and an epoxy resin curing agent.

12. The composition of matters as defined in above 11, wherein the epoxy resin curing agent is at least one member selected from the group consisting of a cationic polymerization initiator, an acid anhydride-based curing agent and a phenol curing agent.

13. An optical electronic member using the adamantane derivative as defined in any one of above 1 to 4, the epoxy compound as defined in above 5, the oxetane compound as defined in above 6, the composition as defined in above 11 or the composition as defined in above 12.

14. A sealant for an electronic circuit using the adamantane derivative as defined in any one of above 1 to 4, the epoxy compound as defined in above 5, the oxetane compound as defined in above 6, the composition as defined in above 11 or the composition as defined in above 12.

Effect of the Invention

An adamantane derivative, an epoxy compound and an oxetane compound having an adamantane skeleton, and compositions containing them are capable of providing a cured product which has excellent optical properties such as transparency and light resistance, long-term heat resistance and electric characteristics such as dielectric permittivity and which can be suitably used as a sealant for an electronic circuit (such as a sealant for an optical semiconductor or an organic electroluminescence (EL) device), as an optical electronic member (such as an optical wave guide, an optical communication lens or an optical film) and as an adhesive for them.

Namely, in the present invention, by introducing an alkyl or alkoxy group or groups into the aromatic ring or rings of the cyclic ether derivative of an adamantane-containing phenol-type compound having excellent heat resistance, transparency and low dielectric permittivity, it is possible to further improve the heat resistance thereof and to impart practically required solubility thereto. When the aromatic ring of the cyclic ether derivative of an adamantane-containing phenol-type compound is a polycyclic aromatic ring, the heat resistance thereof can be further improved and practically required solubility can be imparted thereto.

BEST MODE FOR CARRYING OUT THE INVENTION

The adamantane derivative of the present invention is represented by the following general formula (I):

[Chemical Formula 9]

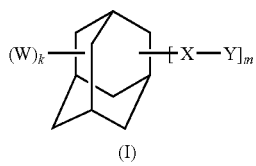

(I)

In the above formula, W represents a group selected from an alkyl group, a halogen atom, a hydroxyl group and =O formed by two W's taken together. The alkyl group represented by W may be straight-chained, branched or cyclic. To be more specific, the alkyl group may be, for example, a methyl group, an ethyl group, a propyl group, a butyl group or a cyclohexyl group. As the halogen atom, there may be mentioned fluorine, chlorine, bromine and iodine.

In the above general formula (I), X represents a group represented by the following general formula (II), (III) or (IV):

[Chemical Formula 10]

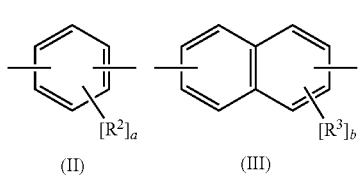

(II)    (III)

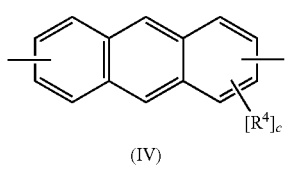

(IV)

In the above formulas, $R^2$ to $R^4$ each independently represent a $C_1$ to $C_{10}$ hydrocarbon group which may contain an oxygen atom or a sulfur atom. As the $C_1$ to $C_{10}$ hydrocarbon group, there may be mentioned an alkyl group. Specific examples of the alkyl group are as given above. Examples of the hydrocarbon group containing an oxygen atom or a sulfur atom include a methoxy group, an ethoxy group, a butoxy group, a hydroxymethyl group, a hydroxyethyl group, a methylthio group and an ethylthio group. The symbol a represents an integer of 1 to 4, preferably 1 or 2, b represents an integer of 0 to 6, preferably 0 to 2 and c represents an integer of 0 to 8, preferably 0 to 2.

In the above general formula (I), Y represents a group represented by the following formula (V) or the following general formula (VI):

[Chemical Formula 11]

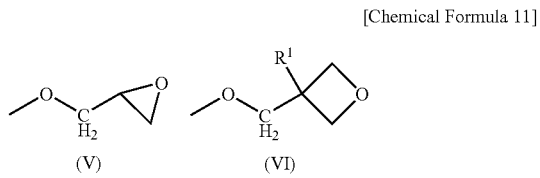

(V)    (VI)

In the formula, $R^1$ represents a methyl group or an ethyl group. In the above general formula (I), m represents an integer of 2 to 4 and k represents an integer of 0 to (16−m), with m being preferably 2.

As the adamantane derivative of the present invention, there may be mentioned, for example, an adamantane derivative in which X in the general formula (I) is attached to a bridge-head carbon of the adamantane skeleton, an adamantane derivative in which, in the general formula (I), m is 2 and each X is attached to the same methylene carbon, and an adamantane derivative in which X is a group represented by the above general formula (II). The adamantane derivative represented by the above general formula (I) preferably has a total chlorine content of 2,000 ppm by mass or less, more preferably 1,000 ppm by mass or less, still more preferably 600 ppm by mass or less. The term "total chlorine content" as used herein is intended to refer to a chlorine content including hydrolyzable chlorine and free chlorine ions.

The adamantane derivative represented by the above general formula (I) is a compound in which adamantane having excellent heat resistance and transparency is linked to a cyclic ether group through a linking group containing an aromatic ring. As a consequence of this structure, not only the heat resistance and transparency but also light resistance and dielectric permittivity are improved. In addition, practically required solubility can be imparted. Further, when the aromatic ring is a polycyclic aromatic ring, the heat resistance can be further improved while maintaining the practically required solubility as is.

The adamantane derivative represented by the above general formula (I) may be synthesized by, for example, reacting a phenolic hydroxyl group-containing adamantane derivative represented by the following general formula (a):

[Chemical Formula 12]

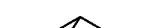

(a)

(wherein W, X, k and m have the same meanings as above) with a reactive cyclic ether compound represented by the following general formula (b):

Y'-D    (b)

in the presence of an alkaline catalyst (Synthesis method (1)).

In the general formula (b), Y' represents a group represented by the following formula (V') or the following general formula (VI'):

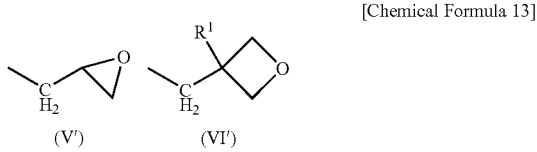

[Chemical Formula 13]

(V')     (VI')

(where R¹ represents a methyl group or an ethyl group) and D represents a group reactive with the phenolic hydroxyl group. Specific examples of the group D include Cl, Br, I, OTs (tosyloxy group) and OMs (mesyloxy group).

The phenolic hydroxyl group-containing adamantane derivative represented by the above general formula (a) may be synthesized by reacting the corresponding adamantane compound with a phenolic hydroxyl group-containing compound in the presence of an acidic catalyst. To perform the reaction, a mercaptan compound may be added as a promoter.

As the adamantane compound, there may be mentioned 1,3-adamantanediol, 1,3,5-adamantanetriol, 1,3,5,7-adamantanetetraol, 2-adamantanone, 4-hydroxy-2-adamantanone and 5-hydroxy-2-adamantanone.

As the phenolic hydroxyl group-containing compound, there may be mentioned alkylphenol compounds such as cresols, 2-t-butylphenol, 2,6-dimethylphenol and 2,4-dimethylphenol; alkoxyphenols such as p-methoxyphenol; polycyclic aromatic hydroxyl compounds such as 1-naphthol, 2-naphthol and 2-hydroxyanthracene; and derivatives of these compounds obtained by introducing an alkyl group, alkoxy group, etc. into the aromatic ring of these compounds.

As the acidic catalyst, there may be mentioned, for example, sulfuric acid, boron trifluoride and tin tetrachloride. The acidic catalyst is generally used in an amount of about 0.1 to about 100 mol %, preferably 1 to 50 mol %, based on the adamantane compound.

As the mercaptan compound, there may be mentioned $C_1$ to $C_{10}$ alkyl mercaptans such as methyl mercaptan, ethyl mercaptan, n-propyl mercaptan, isopropyl mercaptan, n-butyl mercaptan, sec-butyl mercaptan, t-butyl mercaptan, pentyl mercaptan, hexyl mercaptan, heptyl mercaptan, octyl mercaptan, nonyl mercaptan and decyl mercaptan. The mercaptan compound is generally used in an amount of about 0 to about 200 mol %, preferably 0 to 100 mol %, based on the acidic catalyst.

The reaction temperature of the above synthesis is generally about 0 to about 200° C., desirably 20 to 150° C. The reaction pressure in terms of absolute pressure is generally about 0.01 to about 10 MPa, desirably ambient pressure to 1 MPa. The reaction time is generally about 1 minute to about 24 hours, desirably 0.5 to 10 hours.

As the phenolic hydroxyl group-containing adamantane derivative represented by the above general formula (a) thus synthesized, there may be mentioned, for example, adamantane bisalkylphenols such as 1,3-bis(3-methyl-4-hydroxyphenyl)adamantane and 2,2-bis(3-methyl-4-hydroxyphenyl)adamantane; adamantane bisalkoxyphenols such as 1,3-bis(3-methoxy-4-hydroxyphenyl)adamantane and 2,2-bis(3-methoxy-4-hydroxyphenyl)adamantane; adamantane bisnaphthols such as 1,3-bis(6-hydroxynaphthyl)adamantane and 2,2-bis(6-hydroxynaphthyl)adamantane; and adamantane bishydroxyanthracenes such as 1,3-bis(7-hydroxyanthranyl) adamantane and 2,2-bis(7-hydroxyanthranyl) adamantane.

The reaction of a phenolic hydroxyl group-containing adamantane derivative represented by the above general formula (a) with a reactive cyclic ether compound represented by the above general formula (b) is carried out at a temperature of generally about 0 to about 200° C., desirably 20 to 150° C. When the reaction temperature is 0° C. or above, the reaction rate does not decrease and remains moderate so that the reaction time is shortened. When the reaction temperature is 200° C. or below, coloring of the product may be suppressed. The reaction pressure in terms of absolute pressure is about 0.01 to about 10 MPa, desirably ambient pressure to 1 MPa. When the reaction pressure is 10 MPa or less, special equipment is not necessary because the safety is secured. This is advantageous from an industrial point of view. The reaction time is generally about 1 minute to about 24 hours, preferably 1 to 10 hours.

The above reaction is carried out in the presence of a basic catalyst. As the basic catalyst, there may be mentioned sodium amide, triethylamine, tributylamine, trioctylamine, pyridine, N,N-dimethylaniline, 1,5-diazabicyclo[4.3.0]nonene-5 (DBN), 1,8-diazableyclo[5.4.0]undecene-7 (DBU), sodium hydroxide, potassium hydroxide, sodium hydride, sodium phosphate, potassium phosphate, sodium carbonate, potassium carbonate, silver oxide, sodium methoxide and potassium t-butoxide.

The using amount of the basic catalyst relative to a reaction raw material is such that the molar ratio of the basic catalyst to the active hydrogen of the raw material monomer is about 0.8 to about 10, preferably 1 to 5.

When carrying out the above reaction, a quaternary ammonium salt such as tetramethylammonium chloride or tetraethylammonium bromide may be added as a phase transfer catalyst. The using amount of the quaternary ammonium salt is about 0.01 to about 20 mol %, preferably 0.1 to 10 mol %, relative to the phenolic hydroxyl group-containing adamantane derivative.

The reaction is carried out in the absence or presence of a solvent. Advantageously used is a solvent in which the solubility of the above phenolic hydroxyl group-containing adamantane derivative is 0.5% by mass or more, preferably 5% by mass or more. The solvent is used in such an amount as to provide a concentration of the above phenolic hydroxyl group-containing adamantane of 0.5% by mass or more, preferably 5% by mass or more. In this case, the above phenolic hydroxyl group-containing adamantane is preferably in a dissolved state, though it may exist in a suspended state. Specific examples of the solvent include hexane, heptane, toluene, DMF (dimethylformamide), DMAc (N,N-dimethylacetamide), DMSO (dimethylsulfoxide), ethyl acetate, diethyl ether, MIBK (methyl isobutyl ketone) and THF (tetrahydrofuran). These solvents may be used singly or in combination of two or more.

In the above synthesis method (1), it is preferred that the reaction mixture, obtained by reaction of a phenolic hydroxyl group-containing adamantane derivative represented by the above general formula (a) with a reactive cyclic ether compound represented by the above general formula (b), be treated with an alkali metal hydroxide or an alkaline earth metal hydroxide or be subjected to a crystallization process to obtain a purified product, since the resulting adamantane derivative represented by the general formula (I) can have a reduced total chlorine content and show reduced coloring. When the adamantane derivative of the present invention having a small total chlorine content is used in an electric or electronic material, a reduction of electric insulation is less likely to occur and excellent corrosion resistance is obtained.

The alkali metal hydroxide may be, for example, sodium hydroxide or potassium hydroxide. The alkaline earth metal hydroxide may be, for example, magnesium hydroxide or calcium hydroxide. The treatment of the hydroxide may be carried out by, for instance, adding an aqueous hydroxide solution having a concentration of about 1 to about 50% by mass to the reaction mixture, followed by stirring at about 0 to about 120° C. for about 1 minute to about 10 hours.

The crystallization process may be carried out by adding a poor solvent to the reaction mixture, followed by cooling at about −20 to about 50° C. As the poor solvent, there may be mentioned, for example, isopropyl ether, toluene, hexane and methanol. These solvents may be used singly or in combination of two or more thereof.

The above alkali treatment and crystallization may be performed singly or in combination. Further, these processes may be combined with another purifying process such as distillation and column chromatography. The purifying process may be selected depending on the nature of the reaction product and the kind of impurities.

The adamantane derivative represented by the above general formula (I) may also synthesized by subjecting the phenolic hydroxyl group-containing adamantane derivative represented by the above general formula (a) and a halohydrin compound to an addition reaction under an acidic condition, followed by a ring-closure reaction in the presence of a basic catalyst (synthesis process (2)).

As the halohydrin compound, there may be mentioned, for example, a compound represented by the following general formula:

[Chemical Formula 14]

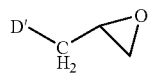

(wherein D' represents Cl, Br or I).

The addition reaction with the halohydrin is generally carried out at a temperature of about 0 to about 100° C., desirably 20 to 85° C. When the reaction temperature is 0° C. or above, the reaction rate does not decrease and remains moderate so that the reaction time is shortened. When the reaction temperature is 100° C. or below, the formation of a by product of a halogen-containing substance may be suppressed. The reaction pressure in terms of absolute pressure is about 0.01 to about 10 MPa, desirably ambient pressure to 1 MPa. When the reaction pressure is 10 MPa or less, special equipment is not necessary because the safety is secured. This is advantageous from an industrial point of view. The reaction time is generally about 1 minute to about 24 hours, desirably 30 minutes to 3 hours.

The above addition reaction is generally carried out in the presence of an acidic catalyst. As the acidic catalyst, there may be mentioned, for example, sulfuric acid, boron trifluoride and tin tetrachloride.

The acidic catalyst is generally used in an amount of about 0.1 to about 20 mol %, preferably 0.5 to 10 mol %, based on the raw material monomer. When the using amount of the acidic catalyst is 20 mol % or less, the formation of a by product of a chlorine-containing substance can be suppressed. With an amount of 0.1 mol % or more, the reaction rate does not decrease but remains moderate so that the reaction time can be reduced.

The reaction is carried out in the absence or presence of a solvent. Advantageously used is a solvent in which the solubility of the above phenolic hydroxyl group-containing adamantane derivative is 0.5% by mass or more, preferably 5% by mass or more. The solvent is used in such an amount as to provide a concentration of the above phenolic hydroxyl group-containing adamantane of 0.5% by mass or more, preferably 5% by mass or more. In this case, the above phenolic hydroxyl group-containing adamantane is preferably in a dissolved state, though it may exist in a suspended state. Specific examples of the solvent include hexane, heptane, toluene, DMF (dimethylformamide), DMAc (N,N-dimethylacetamide), DMSO (dimethylsulfoxide), ethyl acetate, diethyl ether, MIBK (methyl isobutyl ketone) and THF (tetrahydrofuran). These solvents may be used singly or in combination of two or more.

In the synthesis process (2), the above addition reaction is followed by a ring closing reaction in the presence of a basic catalyst. The ring closing reaction is generally carried out at a temperature of about 20 to about 100° C., desirably 30 to 80° C. When the reaction temperature is 20° C. or above, the reaction rate does not decrease and remains moderate so that the reaction time is shortened. When the reaction temperature is 100° C. or below, the formation of a by product can be suppressed and the chlorine content of the obtained adamantane derivative can be reduced. The reaction pressure in terms of absolute pressure is about 0.01 to about 10 MPa, desirably ambient pressure to 1 MPa. When the reaction pressure is 10 MPa or less, special equipment is not necessary because the safety is secured. This is advantageous from an industrial point of view. The reaction time is generally about 1 minute to about 24 hours, desirably 30 minutes to 10 hours.

As the basic catalyst, there may be mentioned sodium hydroxide, potassium hydroxide, sodium phosphate, potassium phosphate, sodium carbonate, potassium carbonate, calcium hydroxide and magnesium hydroxide.

The using amount of the basic catalyst (excluding the amount of the basic catalyst used for neutralization of the acid catalyst used in the addition reaction of the halohydrin compound) is about 1 to about 2 equivalents, preferably 1 to 1.5 equivalents, per hydroxyl group of the raw material monomer. When the using amount of the basic catalyst is 2 equivalents or less, the hydration reaction to a glycidyl ether can be suppressed. With a using amount of 1 equivalent or more, the formation of glycidyl ether by ring closing reaction can proceed sufficiently.

When the addition reaction of the halohydrin compound is carried out using a solvent, the solvent can be used as such. When no solvent is used in the addition reaction, solvents similar to those described above may be used.

In the synthesis process (2) as well, it is preferred that the reaction mixture obtained by reaction of a phenolic hydroxyl group-containing adamantane derivative represented by the above general formula (a) with a halohydrin compound, followed by a ring closing reaction be treated with an alkali metal hydroxide or an alkaline earth metal hydroxide or be subjected to a crystallization process to obtain a purified product in the same way as in the synthesis process (1), since the resulting adamantane derivative represented by the general formula (I) can have a reduced total chlorine content and show reduced coloring. Similar to the synthesis process (1), a plurality of purifying processes can be combined. The purifying process may be selected depending on the nature of the reaction product and the kind of impurities.

When two or more adamantane derivatives represented the above general formula (I) are used as a mixture, the solubility thereof is further improved. An improvement of the solubility may be also obtained when an adamantane derivative represented the above general formula (I) is mixed with another adamantane derivative.

An epoxy compound having an adamantane skeleton represented by the following general formula (VII):

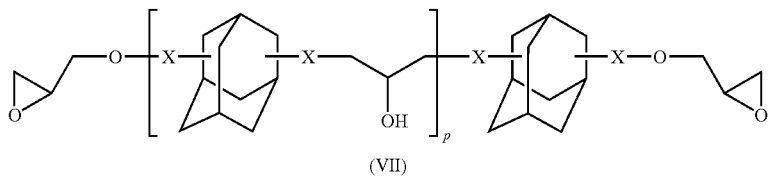

(VII)

or an oxetane compound having an adamantane skeleton represented by the following general formula (VIII):

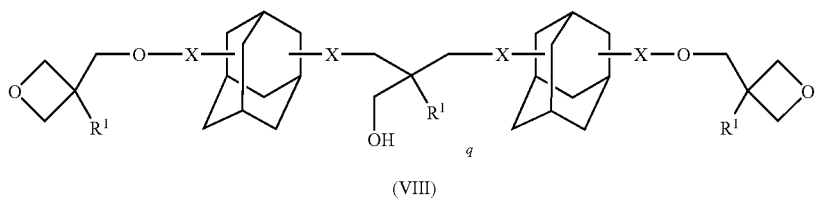

(VIII)

may be obtained without isolating the intended compound from the reaction mixture obtained by the above synthesis process (1) or (2) by further reacting a curable group of the intended compound with a raw material.

In the above general formulas (VII) and (VIII), X represents a group represented by the above general formula (II), (III) or (IV), $R^1$ represents a methyl group or an ethyl group, and p and q are each an integer of 1 to 5. It is preferred that each of the epoxy compound represented by the above general formula (VII) and the oxetane compound represented by the above general formula (VIII) have a total chlorine content of 2,000 ppm by mass or less, more preferably 1,000 ppm by mass or less, still more preferably 600 ppm by mass or less.

A composition of the present invention comprises at least one member selected from an adamantane derivative represented by the above general formula (I), an epoxy compound represented by the above general formula (VII) and an oxetane compound represented by the above general formula (VIII), and an epoxy resin curing agent. In the composition of the present invention, at least one member selected from an adamantane derivative represented by the above general formula (I), an epoxy compound represented by the above general formula (VII) and an oxetane compound represented by the above general formula (VIII) may be used in admixture with other known epoxy resin for best improving the mechanical strength of the cured product as well as the solubility and processability of the composition.

Examples of the known epoxy resin include glycidyl ether epoxy resins such as a bisphenol A epoxy resin, a bisphenol F epoxy resin, a bisphenol 1 epoxy resin, a bisphenol AD epoxy resin, a hydrogenated bisphenol A epoxy resin, a bisphenol G epoxy resin, a tetramethylbisphenol A epoxy resin, a fluorine-containing epoxy resin (e.g. bisphenol AF epoxy resin) and a bisphenol C epoxy resin; novolak epoxy resins such as a phenol novolak epoxy resin and a cresol novolak epoxy resin; alicyclic epoxy resins; nitrogen-containing cyclic epoxy resins such as triglycidyl isocyanurate and a hydantoin epoxy resin; aliphatic epoxy resins; glycidyl ester epoxy resins such as glycidyl (meth)acrylate ester; biphenyl type epoxy resins and dicyclo ring type epoxy resins that become a mainstream of a low water absorption curing type; naphthalene type epoxy resins; and polyfunctional epoxy resins such as trimethylolpropane polyglycidyl ether, glycerol polyglycidyl ether and pentaerythritol polyglycidyl ether. These epoxy resins may be used singly or in a combination of two or more thereof.

The above known epoxy resin may be solid or liquid at room temperature. Generally, however, an epoxy resin having an average epoxy equivalent of 100 to 2,000 is preferred. When the epoxy equivalent is 100 or more, a cured product of the composition of the present invention is not brittle and has a suitable strength. Also, when the epoxy equivalent is 2,000 or less, the glass transition temperature (Tg) of the cured product thereof is not low and is moderate.

The content of at least one member selected from an adamantane derivative represented by the above general formula (I), an epoxy compound represented by the above general formula (VII) and an oxetane compound represented by the above general formula (VIII) in the mixture of the above-described known epoxy resin and at least one member selected from an adamantane derivative represented by the above general formula (I), an epoxy compound represented by the above general formula (VII) and an oxetane compound represented by the above general formula (VIII) is preferably 5% by mass or more, more preferably 10% by mass or more. When the content is 5% by mass or more, the optical characteristics, long-term heat resistance and electric characteristics of the composition of the present invention become satisfactory.

As the curing agent for an epoxy resin contained in the composition of the present invention, there may be mentioned at one member selected from a cationic polymerization initiator, an acid anhydride type curing agent, an amine type curing agent and a phenol type curing agent. Namely, the composition of the present invention may be cured by a reaction using these epoxy resin curing agents.

As the cationic polymerization initiators, those initiators which can react with an epoxy group or an oxetanyl group by heat or UV light may be used. Examples of such initiator include aromatic diazonium salts such as p-methoxybenzenediazonium hexafluorophosphate; aromatic sulfonium salts such as triphenylsulfonium hexafluorophosphate; aromatic iodonium salts such as diphenyliodonium hexafluorophosphate; aromatic iodosyl salts, aromatic sulfoxonium salts; and metallocene compounds. Above all, aromatic sulfonium salts such as triphenylsulfonium hexafluorophosphate, and aromatic iodonium salts such as diphenyliodonium hexafluorophosphate are most suitable. These initiators may be used singly or in a combination of two or more.

The using amount of the cationic polymerization initiator is preferably 0.01 to 5.0 parts by mass, more preferably 0.1 to 3.0 parts by mass, per 100 parts by mass of the mixture of the above-described known epoxy resin and at least one member selected from the above adamantane derivative represented by the general formula (I), the epoxy compound represented by the general formula (VII) and the oxetane compound represented by the general formula (VIII) (the mixture will be hereinafter occasionally referred to as "resin component"). By using the cationic polymerization initiator in an amount within the above range, suitable polymerization may be achieved and good physical properties such as optical characteristics may be expressed.

Examples of the acid anhydride type curing agents include phthalic anhydride, maleic anhydride, trimellitic anhydride, pyromellitic anhydride, hexahydrophthalic anhydride, tetrahydrophthalic anhydride, methylnadic anhydride, nadic anhydride, glutaric anhydride, methylhexahydrophthalic anhydride and methyltetrahydrophthalic anhydride. Above all, hexahydrophthalic anhydride, tetrahydrophthalic anhydride, methylhexahydrophthalic anhydride and methyltetrahydrophthalic anhydride are most suitable. These anhydrides may be used singly or in combination of two or more.

As the phenol type curing agent, there may be mentioned, for example, novolac resins such as a phenol novolac resin, a cresol novolac resin, a bisphenol A novolac resin and a triazine-modified phenol novolac resin. As the amine type curing agent, there may be mentioned, for example, dicyandiamide and aromatic diamines such as m-phenylenediamine, 4,4'-diaminodiphenylmethane, 4,4'-diaminodiphenylsulfone and m-xylylenediamine. These curing agents may be used singly or in a combination of two or more thereof.

Among the above curing agents, the acid anhydride type curing agent and the phenol type curing agent are preferred in view of their physical properties such as transparency and heat resistance. Particularly, hexahydrophthalic anhydride, tetrahydrophthalic anhydride, methylhexahydrophthalic anhydride and methyltetrahydrophthalic anhydride are most preferred.

The blending proportion of the resin component and the curing agent is determined by the ratio of the functional groups of the curing agent that react with the glycidyl group. In general, the blending proportion is such that the functional groups of the corresponding curing agent is 0.5 to 1.5 equivalents, preferably 0.7 to 1.3 equivalents, per equivalent of the glycidyl group. Use of the resin component and the curing agent in a proportion within the above range does not bring about slowing of a curing rate of the composition, lowering of the glass transition temperature of a cured resin or lowering of humidity resistance and, thus, is suitable.

In the present invention, the reaction of the adamantane derivative of the present invention having excellent heat resistance and transparency with the above curing agent results in a further improvement of the heat resistance, transparency, light resistance and, further, dielectric permittivity and, additionally, can impart practically required solubility.

Various customarily employed known additives may be suitably added to the composition of the present invention, if necessary. Examples of the additives include a curing accelerator, a deterioration preventing agent, a modifying agent, a silane coupling agent, a defoaming agent, an inorganic powder, a solvent, a leveling agent, a mold release agent, a dye and a pigment.

The above curing accelerator is not specifically limited and may be, for example, tertiary amines such as 1,8-diaza-bicyclo[5.4.0]undecene-7, triethylenediamine and tris(2,4,6-dimethylaminomethyl)phenol; imidazoles such as 2-ethyl-4-methylimidazole and 2-methylimidazole; phosphorus compounds such as triphenylphosphine, tetraphenylphosphonium bromide, tetraphenylphosphonium tetraphenylborate, tetra-n-butylphosphonium-o, o-diethylphosphorodithioate; quaternary ammonium salts; organometallic salts; and derivatives thereof. These accelerators may be used singly or in a combination of two or more. Among these curing accelerators, the use of a tertiaryamine, an imidazole or a phosphorous compound is preferred.

The content of the curing accelerator is preferably 0.01 to 8.0 parts by mass, more preferably 0.1 to 3.0 parts by mass, per 100 parts by mass of the above resin component. By using the curing accelerator in an amount within the above range, a sufficient curing accelerating effect may be obtained, and coloring of a cured product is not observed.

As the deterioration preventing agent, there may be mentioned customarily known deterioration preventing agents such as a phenol compound, an amine compound, an organic sulfur compound and a phosphorus compound. Addition of the deterioration preventing agent can retain characteristics such as heat resistance and transparency.

Examples of the phenol compounds include commercially available products such as Irganox 1010 (trademark, manufactured by Ciba Specialty Chemicals Inc.), Irganox 1076 (trademark, manufactured by Ciba Specialty Chemicals Inc.), Irganox 1330 (trademark, manufactured by Ciba Specialty Chemicals Inc.), Irganox 3114 (Trademark, manufactured by Ciba Specialty Chemicals Inc.), Irganox 3125 (trademark, manufactured by Ciba Specialty Chemicals Inc.), Irganox 3790 (trademark, manufactured by Ciba Specialty Chemicals Inc.), BHT, Cyanox 1790 (trademark, manufactured by Cyanamid Co.) and Sumilizer GA-80 (trademark, manufactured by Sumitomo Chemical Co., Ltd.).

Examples of the amine compound include Irgastab FS042 (trademark, manufactured by Ciba Specialty Chemicals Inc.), GENOX EP (trademark, manufactured by Crompton Co. Ltd., chemical name: dialkyl-N-methylamine oxide), and hindered amines such as ADK STAB LA-52, LA-57, LA-62, LA-63, LA-67, LA-68, LA-77, LA-82, LA-87 and LA-94 (all manufactured by Asahi Denka Co., Ltd.), Tinuvin 123, 144, 440 and 662 and Chimassorb 2020, 119 and 944 (all manufactured by Ciba Specialty Chemicals Inc.), Hostavin N30 (manufactured by Hoechst GmbH), Cyasorb UV-3346 and UV-3526 (both manufactured by Cytec Industries Inc.), Uval 299 (manufactured by Great Lakes Chemical Corp.), and Sanduvor PR-31 (manufactured by Clariant Corp).

Examples of the organic sulfur compound include commercially available products such as DSTP (Yoshitomi) (trademark, manufactured by Yoshitomi Pharmaceutical Co., Ltd.), DLTP (Yoshitomi) (trademark, manufactured by Yoshitomi Pharmaceutical Co., Ltd.), DLTOIB (trademark, manufactured by Yoshitomi Pharmaceutical Co., Ltd.), DMTP (Yoshitomi) (trademark, manufactured by Yoshitomi Pharmaceutical Co., Ltd.), Seenox 412S (trademark, manufactured by Shipro Kasei, Ltd.) and Cyanox 1212 (trademark, manufactured by Cyanamid Co.).

Examples of the modifying agent include conventionally known modifying agents such as glycols, silicones and alcohols. Examples of the silane coupling agent include conventionally known coupling agents such as silane-type and titanate-type agents. Examples of the defoaming agent include conventionally known defoaming agents such as silicone type agents. Examples of the inorganic powder include conventionally known inorganic powders such as glass powders, silica powders, titania, zinc oxide and alumina, having a particle diameter of several nm to 10 μm depending on the intended use. Examples of the solvent that may be used for epoxy resin powders and as a diluent solvent for coating include aromatic solvents such as toluene and xylene, and ketone solvents such as methyl ethyl ketone, methyl isobutyl ketone and cyclohexanone.

As a method for curing the composition of the present invention, there may be used, for example, a curing method in which the above resin component, an epoxy resin curing agent and various additives are mixed, charged into a mold (resin mold) or formed into a desired shape by coating, and then cured by heating or by irradiating UV rays. In the case of thermal curing, the curing temperature is generally about 50 to about 200° C., preferably 100 to 180° C. A curing temperature of 50° C. or above can prevent curing failure, while a curing temperature of 200° C. or below can prevent coloring. The curing time varies depending on the kind of the resin component, curing agent, curing accelerator and initiator used, but is preferably 0.5 to 6 hours.

The irradiation intensity of the UV rays is generally about 500 to about 5,000 mJ/cm$^2$, preferably 1,000 to 4,000 mJ/cm$^2$. The UV ray irradiation may be followed by heating preferably at 70 to 200° C. for 0.5 to 12 hours.

The molding method is not specifically limited and may be, for example, injection molding, blow molding or press molding. Preferably, however, a molded product is prepared by injection molding of a composition in the form of pellets using an injection molding machine.

The cured product obtained using the resin composition of the present invention is excellent in heat resistance and transparency and can provide a total light transmittance of 70% or more. In addition, as will be seen in the hereinafter described Examples, excellent workability is attained because the dissolution can be carried out at a low temperature. Moreover, it is possible to obtain cured products having high glass transition temperature, excellent durability (heat resistance and light resistance) and good electric characteristics such as dielectric permittivity.

Thus, the composition of the present invention has excellent characteristics and is suitably used as a resin (sealant and adhesive) for an optical semiconductor (e.g. LED), a flat panel display (e.g. organic EL device and liquid crystal), an electronic circuit, an optical circuit (optical wave guide), and for an optical electronic member such as a lens for optical communication or an optical film.

Therefore, the resin composition of the present invention can be used as a semiconductor element or an integrated circuit (IC, etc.), an individual semiconductor (diode, transistor, thermistor, etc.), an LED (LED lamp, chip LED, light receiving element, lens for optical semiconductor, etc.), a sensor (temperature sensor, light sensor, magnetic sensor, etc.), a passive component (high frequency device, resistor, condenser, etc.), a structural component (connector, switch, relay, etc.), an automobile part (circuit system, control system, sensors, lamp seal, etc.), an adhesive (optical component, optical disk, pickup lens, etc.) and, in addition, as an optical film for surface coating.

Therefore, the present invention also provides an optical electronic member, such as a sealant for an optical semiconductor, an optical wave guide, a lens for optical communication, an organic EL device and an optical film, and a sealant for an electronic circuit, using the above-mentioned adamantane derivative, epoxy compound, oxetane compound and composition according to the present invention.

The constitution as a sealant for an optical semiconductor (LED, etc.) may be applied to a bomb shell type device or a surface mount type (SMT) device. The sealant can adhere well to a semiconductor such as GaN formed on a metal or a polyamide and, further, can be used by dispersing therein a fluorescent dye such as YAG. Further, the constitution may also be used for a surface coating material of a bomb shell type LED and for a lens of a SMT type LED.

The constitution for an organic EL can be applied to an organic EL device having a structure composed of anode/positive hole injection layer/luminescent layer/electron injection layer/cathode formed in this order on a transparent substrate such as an ordinary glass or a transparent resin. The constitution as a sealant for an organic EL device may be used as an adhesive to cover an EL device with a resin film coated with a metal can, a metal sheet or SiN, or may directly seal an EL device by dispersing an inorganic filler or the like in the adamantane derivative, epoxy compound, oxetane compound or composition according to the present invention so as to impart a gas-barrier property thereto. The constitution may be also applied to a bottom emission type which is currently a mainstream as a display system. However, when the constitution is applied to a top emission type, which will draw attention in view of the light extraction efficiency in the future, the transparency and heat resistance of the adamantane derivative, epoxy compound, oxetane compound and composition according to the present invention may be effectively utilized.

The constitution for an electronic circuit can be applied as an interlayer insulation film, as an adhesive between a polyimide and a copper foil for a flexible printed board or as a resin for a substrate.

The constitution for an optical circuit can be applied to a thermo-optic switch for a single mode or a multi-mode, an arrayed wave guide grating, an optical multiplex or demultiplexer, a wavelength-variable filter, and a core material or a clad material for an optical fiber. The constitution may also be applied to a micro lens array for focusing a light to a wave guide and a mirror of an MEMS type optical switch. Additionally, the constitution may be applied to a dye binder for a photoelectric transducer.

The constitution for an optical film may be applied for a display as a film substrate for a liquid crystal and as an organic EL film substrate. Alternately, the constitution may be applied to a light diffusion film, an anti-reflection film and a color-converting film by dispersing a fluorescent dye therein.

EXAMPLES

Next, the present invention will be explained in further detail by way of examples, but the invention is not restricted to these examples in any way. In the following Examples and Comparative Examples, the compositions, etc. obtained are evaluated in the following manner.

(1) Glass Transition Temperature

Using a differential scanning calorimeter (DSC-7 manufactured by Perkin Elmer, Inc.), 10 mg of a sample was kept at 50° C. for 5 minutes under a nitrogen atmosphere and then heated at 10° C./minute to obtain a heat flux curve. A discontinuous point observed in the heat flux curve represents a glass transition temperature Tg.

(2) Light Transmittance

A specimen with a thickness of 3 mm was measured in accordance with JIS K7105 at a measuring wavelength of 400 nm (unit: %). A spectrophotometer UV-3100S (manufactured by Shimadzu Corporation) was used as the measuring instrument.

(3) Solubility Test

To 2 g of a sample 1 g of cyclohexanone was added. The mixture was heated to 80° C. to dissolve the sample and cooled to room temperature. Then seed crystals were added thereto and stirred. The solubility (unit: % by mass) of the sample in the solution was measured by liquid chromatography. Such stirring and measurement by liquid chromatography procedures were repeated for about 3 days. The saturation solubility represents the solubility value at which the measured solubility no longer changed.

(4) Compatibility Test with Bisphenol a (BPA) Epoxy Resin

A sample (2.1 g) and 0.9 g of a BPA epoxy resin (Epikote 828 manufactured by Japan Epoxy Resin Co., Ltd.) were heated to 100° C. to 130° C. and mixed. When a uniform mixture was confirmed to be obtained, the mixture was cooled to room temperature and allowed to quiescently stand to observe the precipitation of crystals with naked eyes and to determine the time period required for the crystals to begin precipitating. When the crystals began precipitating within 0 to 2 days, the evaluation was rated "C". When 3 to 6 days were required, the evaluation was rated "B". When no crystals were precipitated even when 7 days had passed, the evaluation was rated "A".

(5) Measurement of Total Chlorine Content

A sample was diluted to a predetermined concentration and combusted using an automatic sample combustion device (model AQF-100 manufactured by Mitsubishi Chemical Corporation). The combustion gas generated was absorbed in an aqueous alkaline solution. Using ion chromatography (DX-120 manufactured by Japan Dionex Co., Ltd), the solution was measured for its chlorine ion concentration, from which a total chlorine content of the sample was determined.

Example 1

Synthesis of 1,3-bis(4-glycidyloxy-3-methylphenyl)adamantane and Purification Thereof (1) Synthesis of 1,3-bis(4-hydroxy-3-methylphenyl)adamantane (BMP13)

In a flask having an inside volume of 100 mL, 8.4 g (50 mmol) of 1,3-adamantanediol, 37 g (400 mmol) of o-cresol and 3.8 g (20 mmol) of p-toluenesulfonic acid monohydrate were charged and heated to 90° C. with stirring. The mixture was heated with stirring for 10 hours until the chromatographic peak of 1,3-adamantanediol disappeared. After completion of the reaction, the reaction mixture was added with 40 mL of toluene and 0.1 g of 85% by mass phosphoric acid and, thereafter, neutralized with a 10% by mass aqueous sodium hydroxide solution. The organic layer was then washed twice with water and cooled so that crystals were precipitated. The crystals were collected by filtration, rinsed with toluene and dried to obtain 14 g (yield: 80%) of BPM13 as white solids.

(2) Synthesis of 1,3-bis(4-glycidyloxy-3-methylphenyl)adamantane (BMP13-EPO)

In a mixed solvent composed of 10 mL of MIBK and 20 mL of DMSO, 7.0 g (20 mmol) of BMP13 obtained in (1) above were dissolved, to which 15 g (162 mmol) of epichlorohydrin were added. The mixture was then heated to 45° C. with stirring, added with 1.75 g (44 mmol) of sodium hydroxide over 0.5 hour, and stirred for another 0.5 hour. Thereafter, the reaction mixture was heated to 65° C. and stirred for 2 hours. The obtained reaction liquid was cooled to room temperature, added with 25 mL of MIBK and washed with water until the aqueous phase became neutralized. Concentration gave 9.5 g of BMP13-EPO-containing yellow viscous liquid (reaction mixture) having a total chlorine content of 3,500 ppm by mass.

(3) Purification of 1,3-bis(4-glycidyloxy-3-methylphenyl)adamantane (BMP13-EPO)

(a) 9.0 Grams of the yellow viscous liquid obtained in (2) above were dissolved in 90 g of MIBK, to which 2 g of a 25% by mass aqueous sodium hydroxide solution were added. The mixture was then heated to 90° C., stirred for 2 hours at 90° C., cooled to room temperature, washed with water until the aqueous phase changed from alkaline to neutral, and further washed twice with water. The reaction liquid was then concentrated to give 8.1 g of BMP13-EPO as light yellow solids having a total chlorine content of 750 ppm by mass and an inorganic chlorine content of 1 ppm by mass.

(b) The light yellow solids (8 g) were dissolved in 8 g of THF, to which 8 g of isopropyl ether (IPE) were added. The mixture was cooled to 0° C. The crystals thus precipitated were collected by filtration and rinsed with IPE to obtain 6.5 g of BMP13-EPO as white solids having a total chlorine content of 300 ppm by mass and an epoxy equivalent of 245. The liquid chromatography revealed that the purity was 94% with the rest being a dimer.

Example 2

Purification of 1,3-bis(4-glycidyloxy-3-methylphenyl)adamantane (BMP13-EPO)

(a) 9.0 Grams of the BMP13-EPO-containing yellow viscous liquid obtained in Example 1(2) were dissolved in 9.0 g of THF, to which 9 g of IPE were added. The mixture was then cooled to 0° C. The precipitated crystals were collected by filtration and rinsed with IPE to obtain 6.3 g of BMP13-EPO as white solids having a total chlorine content of 850 ppm by mass.

(b) 6 Grams of the obtained white solids were dissolved in 60 g of MIBK, to which 1.2 g of a 25% by mass aqueous sodium hydroxide solution were added. The mixture was then heated to 90° C., stirred for 2 hours at 90° C., cooled to room temperature, washed with water until the aqueous phase changed from alkaline to neutral, and further washed twice with water. The reaction liquid was then concentrated to give 5.7 g of BMP13-EPO as white solids having a total chlorine content of 350 ppm by mass and an inorganic chlorine content of 1 ppm by mass. The liquid chromatography revealed that the purity was 93% with the rest being a dimer.

The obtained BMP13-EPO was identified by nuclear magnetic resonance spectra ($^1$H-NMR and $^{13}$C-NMR). The nuclear magnetic resonance spectra were measured with JNM-ECA500 manufactured by JEOL Ltd. using $CDCl_3$ as a solvent.

$^1$H-NMR (500 MHz): 1.77 (m, 2H), 1.91 (m, 8H), 1.96 (m, 2H), 2.25 (s, 6H), 2.28 (m, 2H), 2.78 (m, 2H), 2.90 (t, 2H), 3.35-3.37 (m, 2H), 3.98 (dd, 2H), 4.19 (dd, 2H), 6.76 (d, 2H), 7.15 (d, 2H), 7.17 (s, 2H)

$^{13}$C-NMR (127 MHz): 16.5, 29.8, 36.0, 36.7, 42.6, 44.7, 49.6, 50.4, 69.0, 111.3, 123.0, 126.6, 127.7, 143.5, 154.8

Example 3

Synthesis of 1,3-bis(4-glycidyloxy-3,5-dimethylphenyl)adamantane and Purification Thereof (1) Synthesis of 1,3-bis(4-hydroxy-3,5-dimethylphenyl)adamantine (BDMP13)

The procedures of Example 1(1) were carried out in the same manner as described in Example 1(1) except that 49 g of 2,6-dimethylphenol were used in place of 37 g of o-cresol, thereby obtaining 15 g (yield: 80%) of BDMP13 as white solids.

(2) Synthesis of 1,3-bis(4-glycidyloxy-3,5-dimethylphenyl)adamantane (BDMP13-EPO)

The procedures of Example 1(2) were carried out in the same manner as described in Example 1(2) except that 7.6 g of BDMP13 were used in place of 7.0 g of BMP13, thereby obtaining 10.5 g of yellow viscous liquid containing BDMP13-EPO having a total chlorine content of 3,300 ppm by mass.

(3) Purification of 1,3-bis(4-glycidyloxy-3,5-dimethylphenyl)adamantane (BDMP13-EPO)

The procedures of Example 2 were carried out in the same manner as described in Example 2 except that 10 g of the yellow viscous liquid containing BDMP13-EPO obtained in (2) above were used in place of 9.0 g of the yellow viscous liquid containing BMP13-EPO, thereby obtaining 6.9 g of BDMP13-EPO as white solids having a total chlorine content of 270 ppm by mass and an epoxy equivalent of 259.

The obtained BDMP13-EPO was identified by nuclear magnetic resonance spectra ($^1$H-NMR and $^{13}$C-NMR). The nuclear magnetic resonance spectra were measured with JNM-ECA500 manufactured by JEOL Ltd. using $CDCl_3$ as a solvent.

$^1$H-NMR (500 MHz): 1.76 (m, 2H), 1.90-1.94 (m, 10H), 2.28 (s, 14H), 2.69 (m, 2H), 2.87 (t, 2H), 3.33-3.35 (m, 2H), 3.76 (dd, 2H), 4.00 (dd, 2H), 7.00 (s, 4H)

$^{13}$C-NMR (127 MHz): 16.6, 29.7, 36.0, 36.9, 42.5, 44.7, 49.5, 50.6, 73.2, 125.5, 130.1, 146.4, 153.6

Example 4

Synthesis of 2,2-bis(4-glycidyloxy-3,5-dimethylphenyl)adamantane (BDMP22-EPO) and Purification Thereof (1) Synthesis of 2,2-bis(4-hydroxy-3,5-dimethylphenyl)adamantine (BDMP22)

In a flask having an inside volume of 200 mL, 7.5 g (50 mmol) of 2-adamantanone, 49 g (400 mmol) of 2,6-dimethylphenol and 3.8 g (20 mmol) of p-toluenesulfonic acid monohydrate were charged and heated to 100° C. with stirring. The mixture was heated with stirring for 12 hours until the chromatographic peak of 2-adamantanone disappeared. After completion of the reaction, the reaction mixture was added with 80 mL of toluene and cooled so that crystals were precipitated. The crystals were collected by filtration and rinsed with toluene. Further, the crystals were added with 40 mL of toluene and the mixture was stirred. The thus obtained suspension was filtered. It was confirmed by gas chromatography that no unreacted raw materials were present. The suspension was then dried to obtain 12 g (yield: 64%) of BDMP22 as white solids.

(2) Synthesis of 2,2-bis(4-glycidyloxy-3,5-dimethylphenyl)adamantane (BDMP22-EPO)

In a mixed solvent composed of 10 mL of MIBK and 20 mL of DMSO, 7.6 g (20 mmol) of BDMP22 obtained in (1) above were dissolved, to which 15 g (162 mmol) of epichlorohydrin were added. The mixture was then heated to 45° C. with stirring, added with 1.75 g (44 mmol) of sodium hydroxide over 0.5 hour, and stirred for another 0.5 hour. Thereafter, the reaction mixture was heated to 65° C. and stirred for 2 hours. The obtained reaction liquid was concentrated, added with 150 g of toluene and heated at 100° C. to dissolve the concentrate of the reaction liquid. The toluene solution was cooled to room temperature, filtered to remove insoluble matters and washed with water until the aqueous phase became neutralized. Concentration of the toluene solution gave 9.9 g of BDMP22-EPO-containing yellow viscous liquid (reaction mixture).

(3) Purification of 2,2-bis(4-glycidyloxy-3,5-dimethylphenyl)adamantane (BDMP22-EPO)

The procedures of Example 1(3) were carried out in the same manner as described in Example 1(3) except that 9.0 g of the yellow viscous liquid containing BDMP22-EPO obtained in (2) above were used in place of 9.0 g of the yellow viscous liquid containing BMP13-EPO, thereby obtaining 7.9 g of BDMP22-EPO as white solids having a total chlorine content of 280 ppm by mass.

The obtained BDMP22-EPO was identified by nuclear magnetic resonance spectra ($^1$H-NMR and $^{13}$C-NMR). The nuclear magnetic resonance spectra were measured with JNM-ECA500 manufactured by JEOL Ltd. using $CDCl_3$ as a solvent.

$^1$H-NMR (500 MHz): 1.64-1.69 (m, 6H), 1.76 (s, 2H), 1.99 (d, 4H), 2.21 (s, 12H), 2.66 (dd, 2H), 2.84 (t, 2H), 3.11 (s, 2H), 3.29-3.32 (m, 2H), 3.69 (dd, 2H), 3.95 (dd, 2H), 7.00 (s, 4H)

$^{13}$C-NMR (127 MHz): 16.8, 27.6, 32.1, 33.5, 38.2, 44.7, 49.4, 50.8, 72.9, 126.4, 130.1, 144.0, 152.6

Example 5

Synthesis of 1,3-bis(4-glycidyloxy-3-cyclohexylphenyl)adamantane (BCHP13-EPO) and Purification Thereof (1) Synthesis of 1,3-bis(4-glycidyloxy-3-cyclohexylphenyl) adamantane (BCHP13-EPO)

In a mixed solvent composed of 14 mL of MIBK and 30 mL of DMSO, 10 g (20.6 mmol) of 1,3-bis(4-hydroxy-3-cyclohexylphenyl)adamantane (product of Honshu Chemical Industry Co., Ltd.) were dissolved, to which 15 g of epichlorohydrin were added. The mixture was then heated to 45° C. with stirring, added with 2.0 g (50 mmol) of sodium hydroxide over 0.5 hour, and further stirred for 6 hours. Thereafter, the obtained reaction liquid was cooled to room temperature and added with 50 mL of MIBK. The organic layer was washed with 50 mL of pure water, then one time with 50 mL of 0.1 mol/L hydrochloric acid and twice with 50 mL of pure water. The organic phase was separated and concentrated to give 12.2 g of yellow viscous liquid containing BCHP13-EPO.

(2) Purification of 1,3-bis(4-glycidyloxy-3-cyclohexylphenyl)adamantane (BCHP13-EPO)

In 100 mL of MIBK 10.0 g of the yellow viscous product obtained in (1) above were dissolved, to which 2.2 g of a 25% by mass aqueous sodium hydroxide solution were added. The mixture was then heated to 90° C., stirred for 2 hours at 90° C., cooled to room temperature, washed with water until the aqueous phase changed from alkaline to neutral, and further washed twice with water. The reaction liquid was then concentrated to give 9.6 g of BCH13-EPO as a light yellow viscous product having a total chlorine content of 830 ppm by mass and an epoxy equivalent of 335.

The obtained BCHP13-EPO was identified by nuclear magnetic resonance spectra ($^1$H-NMR and $^{13}$C-NMR). The nuclear magnetic resonance spectra were measured with JNM-ECA500 manufactured by JEOL Ltd. using CDCl$_3$ as a solvent.

$^1$H-NMR (500 MHz): 1.27-1.44 (m, 12H), 1.75-1.97 (m, 20H), 2.28 (s, 2H) 2.75 (dd, 2H), 2.86 (t, 2H), 2.95 (m, 2H), 3.32 (m, 2H), 3.95 (dd, 2H), 4.20 (dd, 2H), 6.78 (d, 2H), 7.13 (dd, 2H), 7.22 (d, 2H)

$^{13}$C-NMR (125 MHz): 26.4, 27.1, 29.7, 33.2, 35.9, 36.9, 37.6, 42.5, 44.5, 49.5, 50.4, 68.7, 111.3, 122.6, 123.4, 135.9, 143.4, 153.7

Total chlorine contents of the adamantane derivatives obtained in above Example 1(2), Example 1(3), Example 2, Example 3(2), Example 3(3), Example 4(3) and Example 5(2) and a total chlorine content of a commercially available low-chlorine content BPA type epoxy resin (Epikote 828US manufactured by Japan Epoxy Resin Inc.) are shown in Table 1.

octanoic acid salt of 1,8-diazabicyclo[5.4.0]undecene-7 (Trade name: SA102, manufactured by San-Apro Ltd.) as a curing accelerator were mixed at room temperature and defoamed to obtain a resin composition. The resin composition was heated at 120° C. for 2 hours and then at 150° C. for another 2 hours to obtain a cured resin product (sheet with a thickness of 3 mm). The physical properties of the obtained cured resin product were as shown in Table 2.

Example 7

1 Gram of BDMP13-EPO (epoxy equivalent: 259) obtained in Example 3 (3), 0.65 g of methylhexahydrophthalic anhydride (Trade name: MH700, manufactured by New Japan Chemical Co., Ltd.) as an acid anhydride and 0.01 g of an octanoic acid salt of 1,8-diazabicyclo[5.4.0]undecene-7 (Trade name: SA102, manufactured by San-Apro Ltd.) as a curing accelerator were mixed at room temperature and defoamed to obtain a resin composition. The resin composition was heated at 120° C. for 2 hours and then at 150° C. for another 2 hours to obtain a cured resin product (sheet with a thickness of 3 mm). The physical properties of the obtained cured resin product were as shown in Table 2.

Example 8

A blend (epoxy equivalent: 246) of 0.5 g of BDMP13-EPO obtained in Example 3(3) and 0.5 g of 1,3-bis(glycidyloxyphenyl)adamantane (BP13-EPO) prepared by a method described in Preparation Examples 3 and 4 of Japanese Unexamined Patent Application Publication No. 2003-321530, 0.68 g of methylhexahydrophthalic anhydride (Trade name: MH700, manufactured by New Japan Chemical Co., Ltd.) as an acid anhydride and 0.01 g of an octanoic acid salt of 1,8-diazabicyclo[5.4.0]undecene-7 (Trade name: SA102, manufactured by San-Apro Ltd.) as a curing accelerator were mixed at room temperature and defoamed to obtain a resin composition. The resin composition was heated at 120° C. for 2 hours and then at 150° C. for another 2 hours to obtain a cured resin product (sheet with a thickness of 3 mm). The physical properties of the obtained cured resin product were as shown in Table 2.

TABLE 1

| | | Example | | | | | | | | Commercially available product |
|---|---|---|---|---|---|---|---|---|---|---|
| | | 1(3) | | 2 | | | | | | |
| | 1(2) | (a) | (b) | (a) | (b) | 3(2) | 3(3) | 4(3) | 5(2) | |
| Adamantane derivative | | BMP13-EPO | | | | BDMP13-EPO | | BDMP22-EPO | BCHP13-EPO | |
| BPA type epoxy resin | | | | | | | | | | Epikote 828US |
| Purifying treatment — Alkali treatment | NO | YES | YES | NO | YES | NO | YES | YES | YES | — |
| Purifying treatment — Crystallization | NO | NO | YES | YES | YES | NO | YES | YES | NO | — |
| Total chlorine content of adamantane derivative (ppm by mass) | 3500 | 750 | 300 | 850 | 350 | 3300 | 270 | 280 | 830 | 1100 |

Example 6

1 Gram of BMP13-EPO (epoxy equivalent: 245) obtained in Example 1(3), 0.68 g of methylhexahydrophthalic anhydride (Trade name: MH700, manufactured by New Japan Chemical Co., Ltd.) as an acid anhydride and 0.01 g of an Example 9

1 Gram of BDMP22-EPO (epoxy equivalent: 256) obtained in Example 4(3), 0.64 g of methylhexahydrophthalic anhydride (Trade name: MH700, manufactured by New Japan Chemical Co., Ltd.) as an acid anhydride and 0.01 g of an octanoic acid salt of 1,8-diazabicyclo[5.4.0]undecene-7 (Trade name: SA102, manufactured by San-Apro Ltd.) as a curing accelerator were mixed at room temperature and defoamed to obtain a resin composition. The resin composition was heated at 120° C. for 2 hours and then at 150° C. for another 2 hours to obtain a cured resin product (sheet with a thickness of 3 mm). The physical properties of the obtained cured resin product were as shown in Table 2.

Example 10

1 Gram of BCHP13-EPO (epoxy equivalent: 335) obtained in Example 5(2), 0.49 g of methylhexahydrophthalic anhydride (Trade name: MH700, manufactured by New Japan Chemical Co., Ltd.) as an acid anhydride and 0.01 g of an octanoic acid salt of 1,8-diazabicyclo[5.4.0]undecene-7 (Trade name: SA102, manufactured by San-Apro Ltd.) as a curing accelerator were mixed at room temperature and defoamed to obtain a resin composition. The resin composition was heated at 120° C. for 2 hours and then at 150° C. for another 2 hours to obtain a cured resin product (sheet with a thickness of 3 mm). The physical properties of the obtained cured resin product were as shown in Table 2.

Comparative Example 1

The procedures of Example 6 were carried out in the same manner as described in Example 6 except that 1,3-bis(glycidyloxyphenyl)adamantane (BP13-EPO) having an epoxy equivalent of 233 was used in place of BMP13-EPO and that the using amount of methylhexahydrophthalic anhydride was changed to 0.72 g, thereby obtaining a cured resin product. The physical properties of the obtained cured resin product were as shown in Table 2.

Comparative Example 2

The procedures of Example 6 were carried out in the same manner as described in Example 6 except that BPA epoxy resin having an epoxy equivalent of 185 was used in place of BMP13-EPO and that the using amount of methylhexahydrophthalic anhydride was changed to 0.91 g, thereby obtaining a cured resin product. The physical properties of the obtained cured resin product were as shown in Table 2.

TABLE 2

|  |  | Example 6 | Example 7 | Example 8 | Example 9 | Example 10 | Comparative Example 1 | Comparative Example 2 |
|---|---|---|---|---|---|---|---|---|
| | | | | | | | | (parts by mass) |
| Composition | Adamantane derivative | | | | | | | |
| | BMP13-EPO | 100 | | | | | | |
| | BDMP13-EPO | | 100 | 50 | | | | |
| | BP13-EPO | | | 50 | | | 100 | |
| | BDMP22-EPO | | | | 100 | | | |
| | BCHP13-EPO | | | | | 100 | | |
| | BPA type epoxy resin | | | | | | | 100 |
| | Acid anhydride (MH700) | 68 | 65 | 68 | 64 | 49 | 72 | 91 |
| | Curing accelerator (SA102) | 1 | 1 | 1 | 1 | 1 | 1 | 1 |
| Physical properties | Glass transition temperature (° C.) | 175 | 185 | 180 | 205 | 183 | 170 | 130 |
| | Light transmittance (%) | 85 | 84 | 85 | 84 | 86 | 85 | 80 |

Test Example 1

Using BMP13-EPO obtained in Example 1(3), solubility in cyclohexanone and compatibility with a BPA epoxy resin were measured. The evaluation results are shown in Table 3.

Test Example 2

Using BDMP13-EPO obtained in Example 3(3), solubility in cyclohexanone and compatibility with a BPA epoxy resin were measured. The evaluation results are shown in Table 3.

Test Example 3

Using a mixture of 0.5 g of BDMP13-EPO obtained in Example 3(3) and 0.5 g of BP13-EPO prepared by a method described in Preparation Examples 3 and 4 of Japanese Unexamined Patent Application Publication No. 2003-321530, solubility in cyclohexanone and compatibility with a BPA epoxy resin were measured. The saturation solubility in the solubility test was determined as a total of BDMP13-EPO and BP13-EPO in the solution. The evaluation results are shown in Table 3.

Test Example 4

Using BDMP22-EPO obtained in Example 4(3), solubility in cyclohexanone and compatibility with a BPA epoxy resin were measured. The evaluation results are shown in Table 3.

Test Example 5

Using BCHP13-EPO obtained in Example 5(2), solubility in cyclohexanone and compatibility with a BPA epoxy resin were measured. The evaluation results are shown in Table 3.

Comparative Test Example 1

The procedures of Test Example 1 were carried out in the same manner as described in Test Example 1 except that 1,3-bis(glycidyloxyphenyl)adamantane (BP13-EPO) having an epoxy equivalent of 233 was used in place of BMP13-EPO. The evaluation results are shown in Table 3.

Comparative Test Example 2

The solubility in cyclohexanone was measured in the same manner as described in Test Example 1 except that BPA epoxy resin having an epoxy equivalent of 185 was used in place of BMP13-EPO. The evaluation results are shown in Table 3.

TABLE 3

| | Test Example | | | | | Comparative Test Example (parts by mass) | |
|---|---|---|---|---|---|---|---|
| | 1 | 2 | 3 | 4 | 5 | 1 | 2 |
| Adamantane derivative | | | | | | | |
| BMP13-EPO | 100 | | | | | | |
| BDMP13-EPO | | 100 | 50 | | | | |
| BP13-EPO | | | 50 | | | 100 | |
| BDMP22-EPO | | | | 100 | | | |
| BCHP13-EPO | | | | | 100 | | |
| BPA type epoxy resin | | | | | | | 100 |
| Solubility in cyclohexanone (% by mass) | 33 | 35 | 50 | 32 | 46 | 30 | 100* |
| Compatibility with BPA type epoxy resin | B | A | A | B | A | C | — |

*mixed in an arbitrary proportion

INDUSTRIAL APPLICABILITY

The adamantane derivative, epoxy and oxetane compounds having an adamantane skeleton, compositions containing them according to the present invention can provide a cured product having excellent optical properties such as transparency and light resistance, long-term heat resistance and electric characteristics such as dielectric permittivity, and can be used as a sealant for an optical semiconductor, as an optical electronic member, such as an optical wave guide, an optical communication lens, a sealant for an organic EL device or an optical film, and as a sealant for an electronic circuit. They are also useful as a coating material, a sealant and an adhesive for displays such as an organic EL device and a liquid crystal display, for illumination such as LED illumination and for information communication components such as an optical circuit.

The invention claimed is:
1. An adamantane derivative, represented by formula (I):

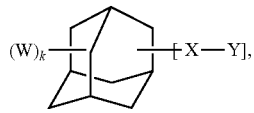

wherein:
m represents an integer of 2 to 4;
k represents an integer of 0 to (16−m);
W represents a group selected from an alkyl group, a halogen atom, a hydroxyl group, and =O formed by two W's taken together;
X is attached to a bridge-head carbon of the adamantane skeleton, and X represents a group represented by formula (II), (III), or (IV):

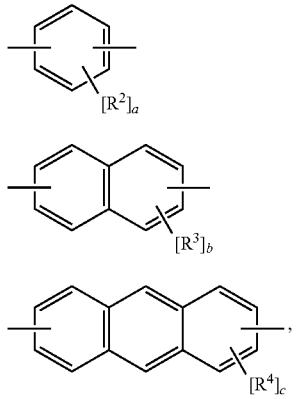

wherein
$R^2$ to $R^4$ each independently represent a $C_1$ to $C_{10}$ hydrocarbon group which may contain an oxygen atom or a sulfur atom,
a represents an integer of 1 to 4,
b represents an integer of 0 to 6, and
c represents an integer of 0 to 8; and
Y represents a group represented by formula (V) or formula (VI):

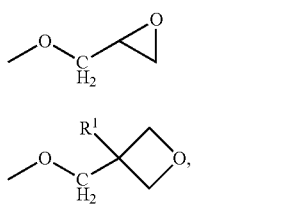

wherein $R^1$ represents a methyl group or an ethyl group.

4. An epoxy compound with an adamantane skeleton, represented by formula (VII):

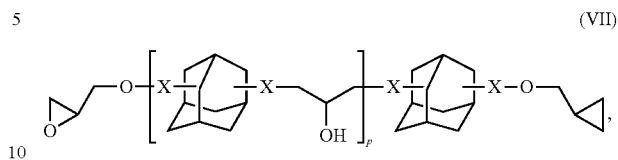

wherein
p represents an integer of 1 to 5, and
X represents a group represented by formula (II), (III) or (IV):

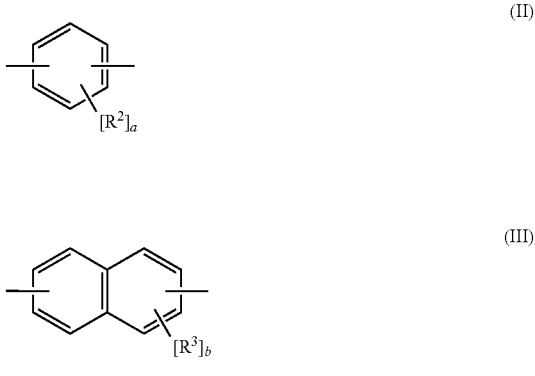

wherein
$R^2$ to $R^4$ each independently represent a $C_1$ to $C_{10}$ hydrocarbon group which may contain an oxygen atom or a sulfur atom,
a represents an integer of 1 to 4,
b represents an integer of 0 to 6, and
c represents an integer of 0 to 8.

5. An oxetane compound with an adamantane skeleton, represented by formula (VIII):

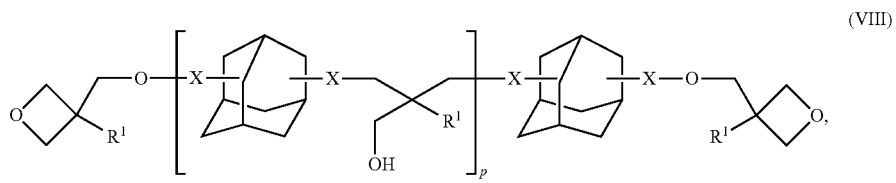

wherein
$R^1$ represents a methyl group or an ethyl group,
q represents an integer of 1 to 5, and
X represents a group represented by formula (II), (III) or (IV):

2. The adamantane derivative as defined in claim 1, wherein, in formula (I), m is 2.

3. The adamantane derivative as defined in claim 1, wherein, in formula (I),
X is a group represented by formula (II).

(II)

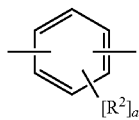

(III)

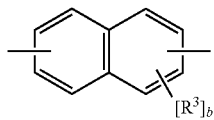

(IV)

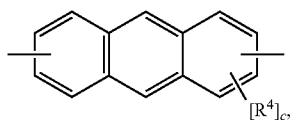

wherein $R^2$ to $R^4$ each independently represent a $C_1$ to $C_{10}$ hydrocarbon group which may contain an oxygen atom or a sulfur atom, a represents an integer of 1 to 4, b represents an integer of 0 to 6, and c represents an integer of 0 to 8.

6. The adamantane derivative as defined in claim 1, having a total chlorine content of 2,000 ppm by mass or less.

7. A process for producing adamantane derivative of claim 1, said process comprising:

(A) reacting a phenolic hydroxyl group-containing adamantane derivative of formula (a):

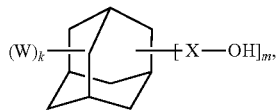
(a)

with a reactive cyclic ether of formula (b):

Y'-D  (b)

wherein

D represents a group reactive with the phenolic hydroxyl group, and

Y' represents a group of formula (V') or formula (VI'):

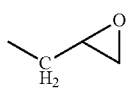
(V')

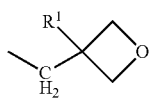
(VI')

wherein $R^1$ represents a methyl group or an ethyl group, in the presence of an alkaline catalyst.

8. The process of claim 7, wherein a reaction mixture obtained by the reaction of the adamantane derivative of formula (a) and the reactive cyclic ether compound of formula (b) is treated with an alkali metal hydroxide or an alkaline earth metal hydroxide.

9. The process of claim 7, wherein a reaction mixture obtained by the reaction of the adamantane derivative of formula (a) and the reactive cyclic ether compound of formula (b) is subjected to crystallization to collect a purified product.

10. A composition of matter, comprising an epoxy resin curing agent and at least one member selected from the group consisting of:

(1) the adamantane derivative of claim 1;

(2) the epoxy compound of formula (VII):

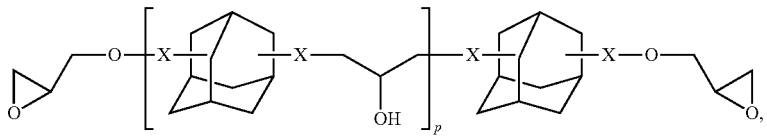
(VII)

wherein p represents an integer of 1 to 5, and

X represents a group represented by formula (II), (III) or (IV):

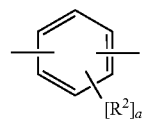
(II)

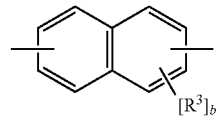
(III)

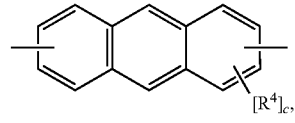
(IV)

wherein $R^2$ to $R^4$ each independently represent a $C_1$ to $C_{10}$ hydrocarbon group which may contain an oxygen atom or a sulfur atom, a represents an integer of 1 to 4, b represents an integer of 0 to 6, and c represents an integer of 0 to 8; and (3) the oxetane compound of formula (VIII):

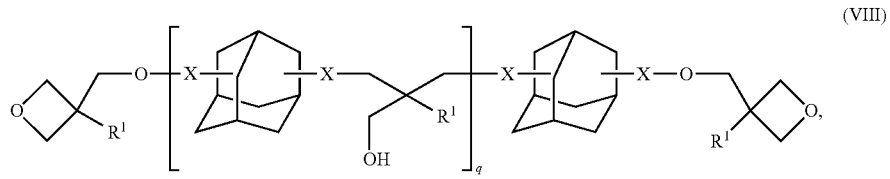

wherein
$R^1$ represents a methyl group or an ethyl group,
q represents an integer of 1 to 5, and
X represents a group represented by formula (II), (III) or (IV):

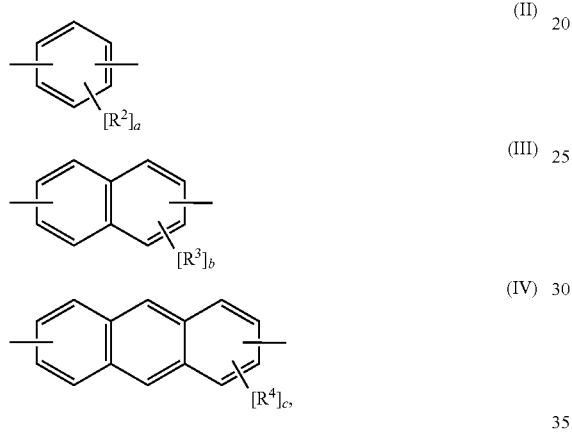

wherein
$R^2$ to $R^4$ each independently represent a $C_1$ to $C_{10}$ hydrocarbon group which may contain an oxygen atom or a sulfur atom,
a represents an integer of 1 to 4,
b represents an integer of 0 to 6, and
c represents an integer of 0 to 8.

11. The composition of in claim 10, wherein the epoxy resin curing agent is at least one member selected from the group consisting of a cationic polymerization initiator, an acid anhydride-based curing agent, and a phenol curing agent.

12. An optical electronic member comprising:
(a) the adamantane derivative of claim 1;
(b) the epoxy compound of formula (VII):

wherein
p represents an integer of 1 to 5, and
X represents a group represented by formula (II), (III) or (IV):

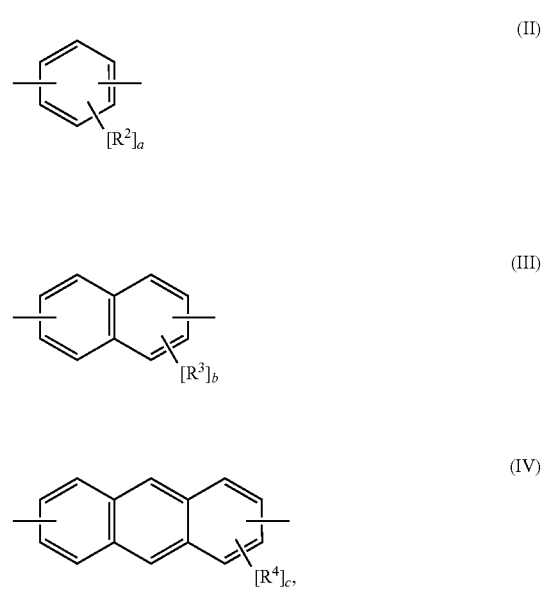

wherein
$R^2$ to $R^4$ each independently represent a $C_1$ to $C_{10}$ hydrocarbon group which may contain an oxygen atom or a sulfur atom,
a represents an integer of 1 to 4,
b represents an integer of 0 to 6, and
c represents an integer of 0 to 8,

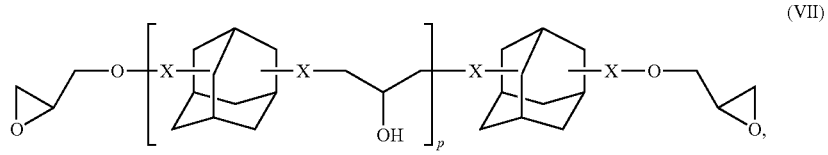

(c) the oxetane compound of formula (VIII):

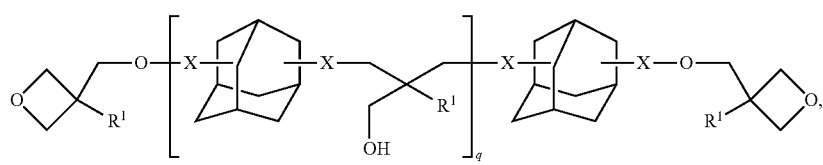

wherein
$R^1$ represents a methyl group or an ethyl group,
q represents an integer of 1 to 5, and
X represents a group represented by formula (II), (III) or (IV):

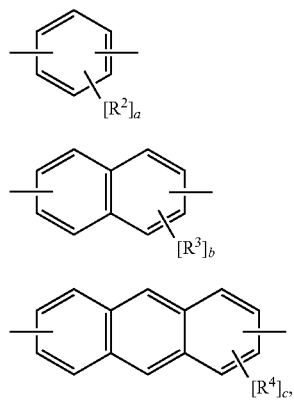

wherein
 $R^2$ to $R^4$ each independently represent a $C_1$ to $C_{10}$ hydrocarbon group which may contain an oxygen atom or a sulfur atom,
 a represents an integer of 1 to 4,
 b represents an integer of 0 to 6, and
 c represents an integer of 0 to 8;
(d) the composition an epoxy resin curing agent and at least one member selected from the group consisting of the adamantane derivative (a), the epoxy compound (b), and the oxetane compound (c); or
(e) the composition of (d), wherein the epoxy resin curing agent is at least one member selected from the group consisting of a cationic polymerization initiator, an acid anhydride-based curing agent, and a phenol curing agent.

13. A sealant for an electronic circuit, comprising:
(a) the adamantane derivative of claim 1;
(b) the epoxy compound of formula (VII):

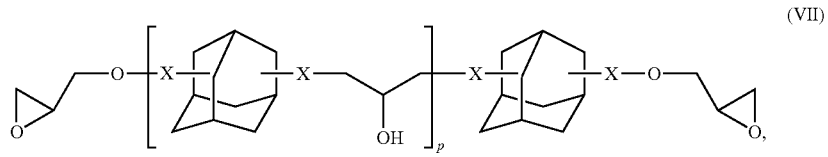

wherein
p represents an integer of 1 to 5, and
X represents a group represented by formula (II), (III) or (IV):

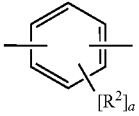

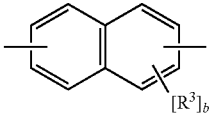

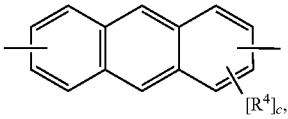

wherein
 $R^2$ to $R^4$ each independently represent a $C_1$ to $C_{10}$ hydrocarbon group which may contain an oxygen atom or a sulfur atom,
 a represents an integer of 1 to 4,
 b represents an integer of 0 to 6, and
 c represents an integer of 0 to 8;
(c) the oxetane compound of formula (VIII):

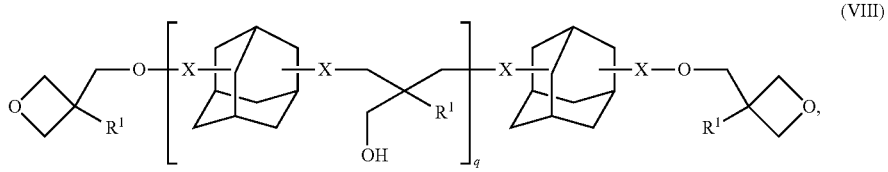

wherein
R$^1$ represents a methyl group or an ethyl group,
q represents an integer of 1 to 5, and
X represents a group represented by formula (II), (III) or (IV):

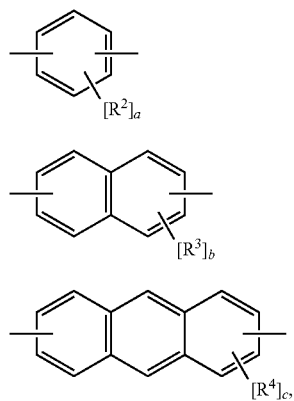

wherein
R$^2$ to R$^4$ each independently represent a C$_1$ to C$_{10}$ hydrocarbon group which may contain an oxygen atom or a sulfur atom, a represents an integer of 1 to 4,
b represents an integer of 0 to 6, and
c represents an integer of 0 to 8;

(d) the composition an epoxy resin curing agent and at least one member selected from the group consisting of the adamantane derivative (a), the epoxy compound (b), and the oxetane compound (c); or (e) the composition (d), wherein the epoxy resin curing agent is at least one member selected from the group consisting of a cationic polymerization initiator, an acid anhydride-based curing agent, and a phenol curing agent.

14. The epoxy compound as defined in claim 4, having a total chlorine content of 2,000 ppm by mass or less.

15. The oxetane compound as defined in claim 5, having a total chlorine content of 2,000 ppm by mass or less.

16. The adamantane derivative as defined in claim 1, wherein, in formula (I), X is represented by formula (III).

17. The adamantane derivative as defined in claim 1, wherein, in formula (I), X is represented by formula (IV).

18. The adamantane derivative as defined in claim 1, wherein, in formula (I), Y is represented by formula (V).

19. The adamantane derivative as defined in claim 1, wherein, in formula (I), Y is represented by formula (VI).

20. The adamantane derivative as defined in claim 1, wherein, in formula (I), m is 3.

* * * * *